(12) United States Patent
Ellis

(10) Patent No.: US 8,591,697 B2
(45) Date of Patent: Nov. 26, 2013

(54) TRANSMISSION ELECTRON MICROSCOPY SAMPLE ETCHING FIXTURE

(75) Inventor: Arthur Wood Ellis, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 6 days.

(21) Appl. No.: 13/360,877

(22) Filed: Jan. 30, 2012

(65) Prior Publication Data

US 2012/0211162 A1 Aug. 23, 2012

Related U.S. Application Data

(62) Division of application No. 12/172,876, filed on Jul. 14, 2008, now Pat. No. 8,105,499.

(51) Int. Cl.
*C23C 16/50* (2006.01)
*C23C 16/00* (2006.01)
*C23F 1/00* (2006.01)
*H01L 21/306* (2006.01)

(52) U.S. Cl.
USPC .............. 156/345.19; 156/345.11; 156/345.3; 118/721

(58) Field of Classification Search
USPC .................. 118/720, 721; 156/345.1, 345.11, 156/345.19, 345.3; 216/12, 41–51; 427/468
See application file for complete search history.

(56) References Cited

U.S. PATENT DOCUMENTS

| 4,101,782 | A | * | 7/1978 | Seliger ..................... 250/492.3 |
| 5,492,566 | A | * | 2/1996 | Sumnitsch .................... 118/500 |
| 6,146,489 | A | * | 11/2000 | Wirth ............................ 156/280 |
| 2001/0013501 | A1 | * | 8/2001 | Rolfson ......................... 216/12 |
| 2005/0112541 | A1 | * | 5/2005 | Durack et al. .................... 435/2 |
| 2008/0266551 | A1 | * | 10/2008 | Araki et al. ..................... 356/73 |

* cited by examiner

*Primary Examiner* — Parviz Hassanzadeh
*Assistant Examiner* — Tiffany Nuckols
(74) *Attorney, Agent, or Firm* — Michael J. Buchenhorner; Vazken Alexanian

(57) ABSTRACT

A mask fixture for etching an item includes: a top fixture disposed over the item, including a reservoir centered within the top fixture for containing an etchant; a bottom fixture underneath the item to be etched including a recessed surface area centered within the bottom fixture; and an etch-resistant window for holding the item to be etched, the etch-resistant window disposed entirely within the recessed surface area. In addtition, a small via centered within and intersecting both the top and bottom fixtures acts as a path for a high intensity light beam.

14 Claims, 3 Drawing Sheets

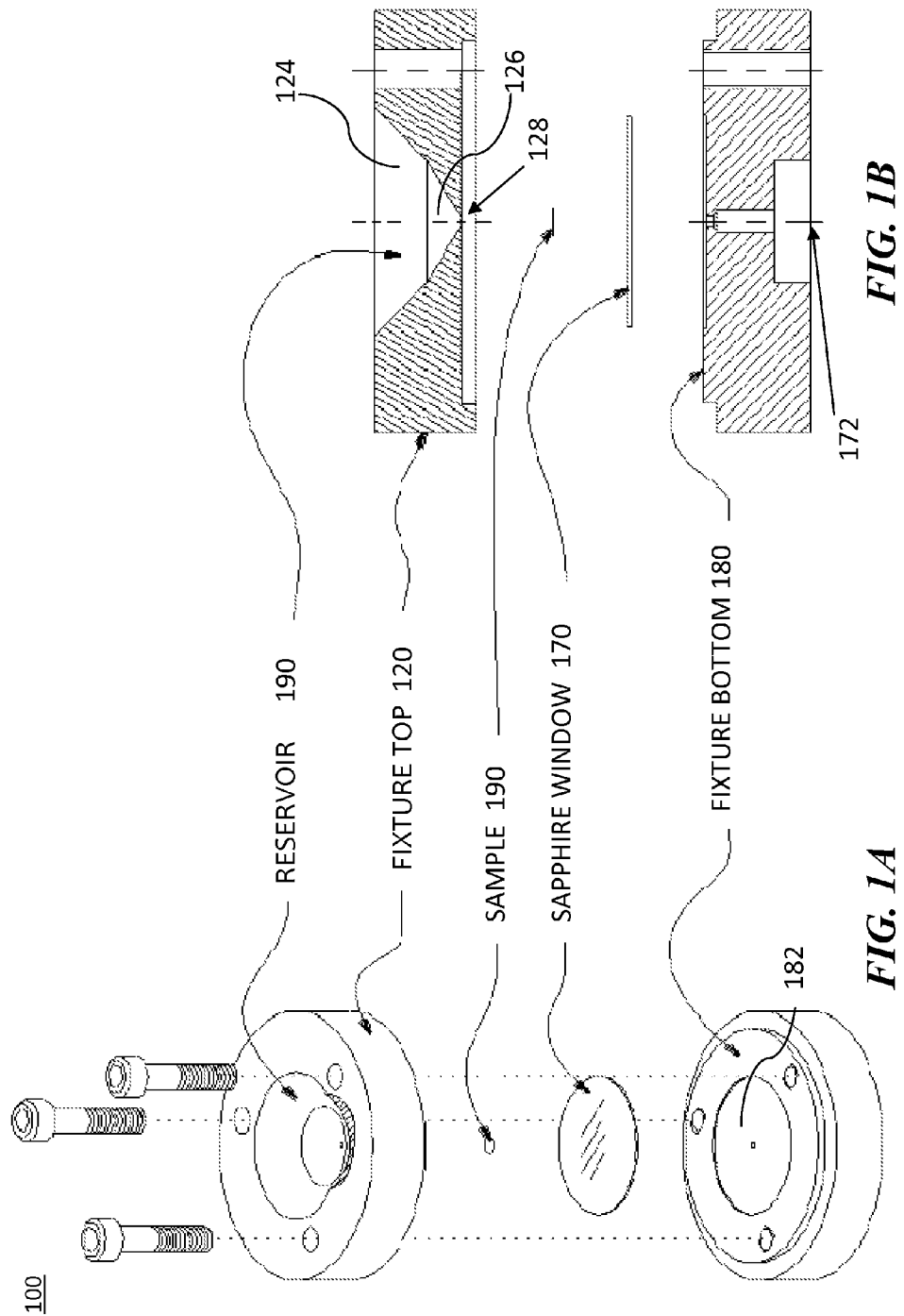

TRANSMISSION ELECTRON MICROSCOPY SAMPLE ETCHING FIXTURE

CROSS-REFERENCE TO RELATED APPLICATIONS

This application is a division of, and claims priority from U.S. patent application Ser. No. 12/172,876, filed on Jul. 14, 2008, which application is incorporated by reference in its entirety herein.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of transmission electron microscopy (TEM) and more particularly relates to the field of TEM sample etching fixtures.

BACKGROUND OF THE INVENTION

During the preparation of transmission electron microscopy (TEM) samples, a mask or template is placed over a sample or specimen to allow a selective area to be eroded through acid etching. One common factor when preparing samples that require the use of highly corrosive etchants has been to use wax to mask the area not to be etched. One such process is the jet etch process where the sample is masked and mounted with wax.

Another procedure is to manually prepare samples which are entirely covered with wax except for the portion to be etched. Because manually prepared samples need little hardware set-up, the costs of the operation are mostly personnel related costs, therefore process steps that can be removed result in money saved. The drawback is the difficulty of monitoring the etch erosion.

In either case, once the etching is complete, the wax or stop-off must be removed with an adequate solvent. For the manual preparation of a common 100 micron thick sample, this process can be rather labor intensive and create chemical waste from both the etchant as well as the solvent used for the mask removal. In the jet etch process, the wax removal cannot be automated because the sample is also mounted using the wax. This necessitates the manual handling of the sample specifically for post etch cleaning.

SUMMARY OF THE INVENTION

Briefly, according to an embodiment of the invention, a mask fixture for etching an item includes: a top fixture disposed over the item, including a reservoir centered within the top fixture for containing an etchant; a bottom fixture underneath the item to be etched including a recessed surface area centered within the bottom fixture; and an etch-resistant window for holding the item to be etched, the etch-resistant window disposed entirely within the recessed surface area. In addition, a small via centered within and intersecting both the top and bottom fixtures acts as a path for a high intensity light beam.

BRIEF DESCRIPTION OF THE DRAWINGS

To describe the foregoing and other exemplary purposes, aspects, and advantages, we use the following detailed description of an exemplary embodiment of the invention with reference to the drawings, in which:

FIG. 1a is an illustration of the mask fixture, showing an oblique view of the three main components of the fixture, according to an embodiment of the present invention;

FIG. 1b is an illustration showing a cross-section view of the top and bottom portions of the fixture, and the sapphire window, according to an embodiment of the present invention;

Figure 2A:
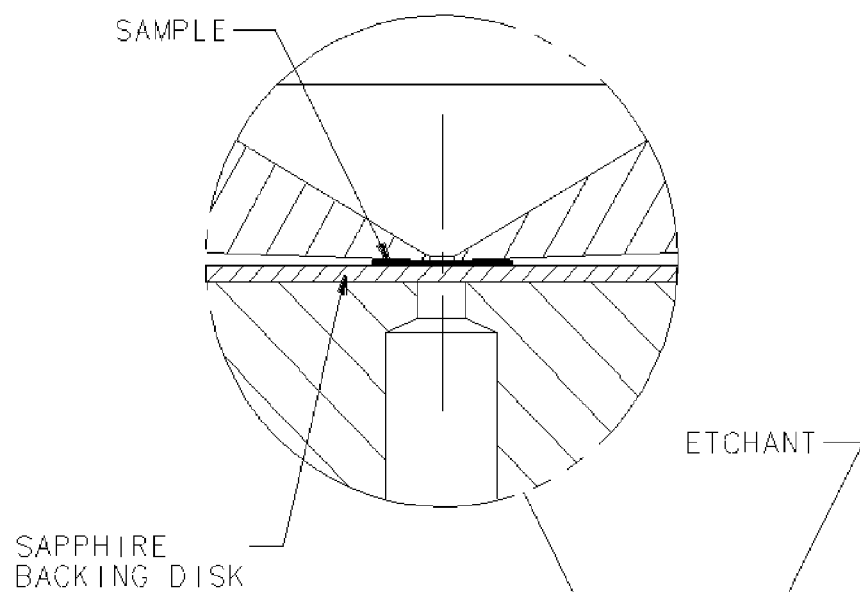
FIG. 2a is a close-up cross-section view of the sample on the sapphire backing disk, according to an embodiment of the present invention.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

We discuss a sample holder for the micro analysis of a sample item. The holder is shaped like a hockey puck, with a top section and a bottom section sandwiching the sample item with a mask, all contained within the hockey puck-shaped holder. This sample holder is a non-consumable mask fixture used for TEM sample preparation. It is clamped about the specimen and is self-sealing, eliminating the need for masking and mounting waxes as well as the solvents needed to remove them. Integral to the fixture is an etch-resistant window to allow in situ observation of the etch progress. When etching certain materials such as silicon, light will begin to be transmitted through the sample as the eroded portion approaches a usable thickness. By providing a path for a high intensity light in the fixture, the transmission of light through the sample can be monitored either manually or automatically.

Referring now in specific detail to the drawings, and particularly FIG. 1, there is illustrated a mask fixture 100 for TEM sample preparation. The specific geometry of the mask fixture 100 is tailored to the thickness of the specimen and the area to be etched. The mask fixture 100 is essentially a three piece fixture: a puck-shaped bottom 180, a puck-shaped top 120 and a sapphire window 170. Note that we discuss a hockey puck, or disc, shape, but those with knowledge in the art will appreciate that other shapes can be advantageously used within the spirit and scope of the invention.

In a preferred embodiment, the puck-shaped base 180 is constructed of PVDF (polyvinylidene fluoride) and is fabricated with a recess 182 which holds an etch-resistant wafer 170 made from sapphire. In other embodiments, the base 180 may be constructed of polytetrafluoroethylene (PTFE), polyethylene, or any other suitable hydrofluoric acid resistant material.

Additionally, the sapphire wafer 170 shown here may be substituted with CVD silicon carbide or CVD glassy carbon film deposited onto a transparent substrate. Other materials may be contemplated that are transparent to visible light. The function of the disc 170 is to protect the sample by providing adequate support when being clamped.

When the etch-resistant wafer 170 is placed in the recess 182, it fills the entire recess 182 and does not extend above the top surface of the bottom fixture 180. This is to facilitate a complete seal when the top and bottom fixtures are secured together. The recess 182 is formed with a small aperture 172, or via, through which light can pass. The aperture 172 extends through the base 180, with the light source emanating from underneath the fixture bottom 180.

When the sapphire 170 is situated within the recess, light is transmitted up through the aperture 172 and through the sapphire window 170. Someone observing from above the fixture 100 with a microscope can tell when the etching of the sample 190 has progressed to the point where the beam of light is visible through the sample 190. This indicates that the sample is at the desired thickness; therefore, the etching is complete.

The top of the fixture 120, also constructed of PVDF and puck-shaped, contains a reservoir 130 for the etchant. Note that the etchant is preferably a liquid etchant, but a powder etchant, and even a gas etchant can also be used, in keeping with the spirit and scope of the invention. The reservoir 130 is made up of two cones. The top cone 124 has a 90 degree inclusive angle and extends to half-way through the puck 120. The second cone 126 has a 120 degree inclusive angle and begins at an intersection of the first cone 124 and terminates with a small hole 128 at the bottom. The small hole 128 is positioned directly in line with the aperture 172 running through the fixture bottom 180, providing a direct line of sight to the light beam emanating up from beneath the fixture bottom 180.

The bottom cone 126 is shallower than the top cone 124 to facilitate the upward release of bubbles as the etching proceeds, when a liquid etchant is used. Below the small aperture 128 in the cone, facing down, the surface of the bottom cone 126 forms a very shallow cone which, when put in assembly, allows the sample 190 to contact the edge of the small aperture 128 first. Upon tightening, this edge is compressed against the sample 190 to a pre-set amount resulting in a fluid-tight seal.

The base 180 and top 120 fixtures can be secured with screws 190 as shown, or with a clamp, or other type of interconnect. This being done, the etchant is applied to the reservoir 130 and flows down through the cone-shaped reservoir 130, through the small aperture 128 and onto the wafer 190. The etch progress can be monitored through a microscope looking down through the reservoir 130 in situ. The illumination is provided by a high intensity light source passing up through the hole 172 in the base puck 180 and through the sapphire 170 on which the sample 190 rests.

Although we limit our examples to visible light being transmitted, other wavelengths could be used for sample specific transmission. The illumination allows an observer to easily determine when the etching process has etched the sample 190 to a desired thickness. The sample 190 may be a silicon wafer, germanium or other similar material. The function of this fixture depends upon the characteristic of silicon and similar materials whereby they begin to become transmissive to light when thinned to tens of microns in thickness.

At completion, the remaining etchant is drained from the reservoir 130 and the sample 190 removed and rinsed without any further solvents or steps necessary. The fixture 100 is immediately ready for the next sample 190. Real savings in labor and equipment are realized in that the only hardware necessary for this process is the etch fixture 100 shown in the illustrations and standard lab equipment such as the microscope and light source.

Referring now to FIG. 2a we provide a close-up cross-section view of the sample 190 situated above the sapphire backing disk or window 170. This close-up view provides a clearer view of the shallow angle where the contact is made with the sample 190 by the shallow cone as previously discussed.

Figure 2B:
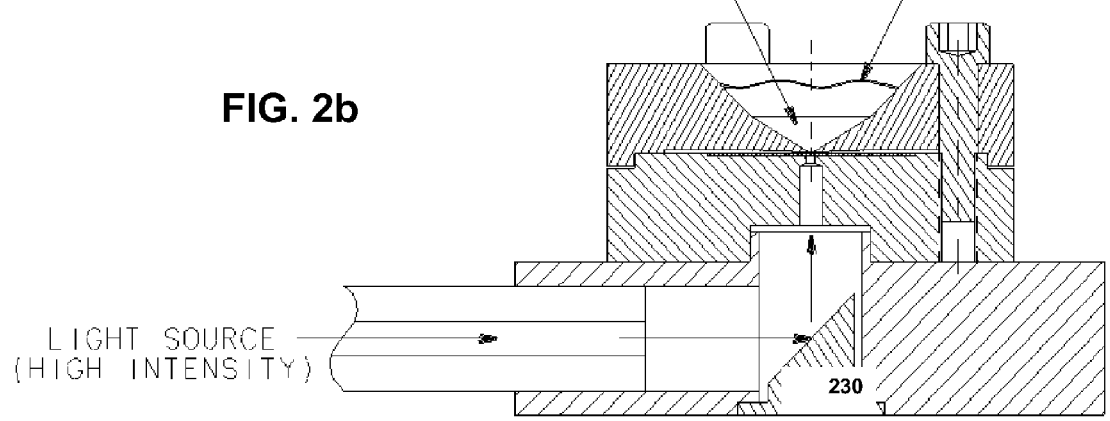
FIG. 2b is a cross-section view showing the different portions of the fixture, according to an embodiment of the present invention.

FIG. 2b is a cross-section view showing the positioning of the different components of the mask fixture, the sample, and the light source. FIG. 2b introduces one optional component of the invention not previously discussed. A mirror 230 is used to re-direct the high intensity light source upwards through the sapphire 170.

Figure 3:
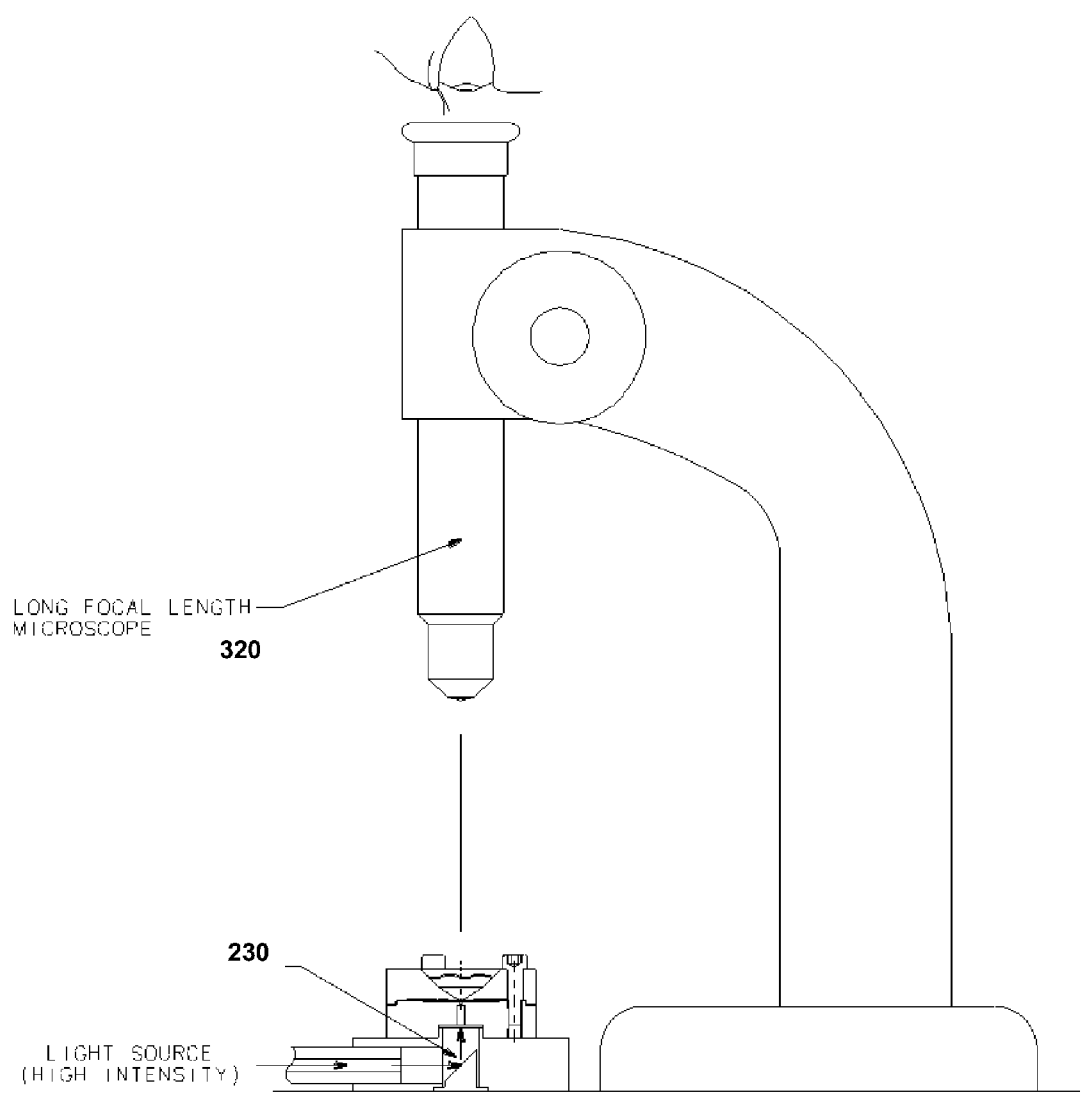
FIG. 3 is an illustration of a person peering through a microscope at the progress of the etching process, according to an embodiment of the present invention.

FIG. 3 shows a viewer peering through a microscope 320 to determine the etching progress. FIG. 3 also shows the mirror 230 used to reflect a light beam or other high intensity light source upwards through the sapphire window 170.

Therefore, while there has been described what is presently considered to be the preferred embodiment, it will understood by those skilled in the art that other modifications can be made within the spirit of the invention. The above description of an embodiment is not intended to be exhaustive or limiting in scope. The embodiment, as described, was chosen in order to explain the principles of the invention, show its practical application, and enable those with ordinary skill in the art to understand how to make and use the invention. It should be understood that the invention is not limited to the embodiments described above, but rather should be interpreted within the full meaning and scope of the appended claims.

I claim:

1. A mask fixture for etching an item, the mask fixture comprising:
    a top fixture disposed over the item, the top fixture comprising a reservoir centered within the top fixture;
    a bottom fixture underneath the item to be etched, the bottom fixture comprising a recessed surface area centered within the bottom fixture;
    an etch-resistant window for holding the item, wherein the etch-resistant window is disposed within the recessed surface area such that the etch-resistant window fits entirely within the recessed surface area and does not extend above the bottom fixture when situated in the recessed surface area;
    a small via centered within and intersecting both the top and bottom fixtures, defining a path for a high intensity light beam;
    a high intensity light source projecting the high intensity light beam upwards through the small via onto the item, wherein said high intensity light beam becomes visible from above, through the etched item, when the item is thinned by the etching to a thickness of tens of microns, thus becoming transmissive to light; and
    an interconnect for coupling the top and bottom fixtures such that a tight seal is created around the item to be etched when the top and bottom fixtures are coupled.

2. The mask fixture of claim 1 wherein the top and bottom fixtures are disc-shaped.

3. The mask fixture of claim 1 wherein the reservoir is shaped like a cone, decreasing in diameter as it nears a bottom surface of the top fixture.

4. The mask fixture of claim 3 wherein the reservoir comprises:
    a first cone comprising a ninety degree inclusive angle and extending to halfway through the top fixture; and a second cone comprising a one-hundred and twenty degree inclusive angle starting from a termination point of the first cone and terminating at a bottom surface of the top fixture.

5. The mask fixture of claim 4 wherein the top fixture further comprises a third shallow cone along the bottom surface of the top fixture terminating at the small via such that, upon sealing the mask fixture, the item to be etched makes contact with the small via, and the third shallow cone is compressed against the item, resulting in a fluid-tight seal.

6. The mask fixture of claim 1 wherein the interconnect comprises screws fitted through holes running through the top and bottom fixtures.

7. The mask fixture of claim 1 wherein the interconnect is a clamp.

8. The mask fixture of claim 1 wherein the etchant is a liquid etchant.

9. The mask fixture of claim 1 wherein the etchant is a powder etchant.

10. The mask fixture of claim 1 wherein the etch-resistant window is formed from sapphire.

11. The mask fixture of claim 1 wherein the top and bottom fixtures are formed from polyvinylidene fluoride.

12. The mask fixture of claim 1 further comprising an angled mirror to reflect the high intensity light source upwards.

13. The mask fixture of claim 1 wherein the reservoir is designed for containing an etchant for etching the item to a desired thickness.

14. The mask fixture of claim 1 further comprising:
a microscope positioned such that a viewer is able to gauge progress of the etching by viewing the etching process through said microscope.

* * * * *